United States Patent [19]

Schroth et al.

[11] Patent Number: 4,608,115

[45] Date of Patent: Aug. 26, 1986

[54] REVOLVING TRANSFER ROLL

[75] Inventors: Carl G. Schroth, Kimberly; Russell E. Thorson, Appleton, both of Wis.

[73] Assignee: Kimberly-Clark Corporation, Neenah, Wis.

[21] Appl. No.: 603,017

[22] Filed: Apr. 23, 1984

[51] Int. Cl.⁴ ............................................. B32B 31/00
[52] U.S. Cl. ................................... 156/519; 156/164; 83/152; 83/154; 83/161
[58] Field of Search ........................ 83/152, 154, 161; 156/519, 521, 164; 198/377

[56] References Cited

U.S. PATENT DOCUMENTS

| 3,728,191 | 4/1973 | Wierzba et al. | 156/292 |
| 4,242,167 | 12/1980 | Hoffmann | 156/521 |
| 4,394,933 | 7/1983 | Ackley | 198/377 |

Primary Examiner—Frank T. Yost
Assistant Examiner—Hien H. Phan
Attorney, Agent, or Firm—Kimberly-Clark Corporation

[57] ABSTRACT

An apparatus including a revolving roll for applying to a sheet of a first material continuously moving in a first direction at least one discrete length of a second material with the length of the discrete length at an angle to the first direction. The discrete length is cut from a continuous ribbon on the revolving roll, rotated by the revolving roll to a desired orientation and transferred from the revolving roll to the sheet. The apparatus includes the revolving roll, at least one rotatable platen on, and revolvable with the revolvable roll, a feeding apparatus for feeding the continuous ribbon to circumferential engagement with the revolving roll, a cutting roll and an applicator roll revolving in synchronizm with the revolving roll. The cutting roll has at least one cutting blade which cuts the ribbon at a cutting surface or anvil on the rotatable platen. The applicator roll, disposed on an opposite side of the sheet, has at least one striking member which strikes the sheet at an area on which the discrete length is to be transferred.

15 Claims, 13 Drawing Figures

REVOLVING TRANSFER ROLL

FIELD OF THE INVENTION

This invention relates to an apparatus for carrying articles on a revolving roll toward a receiving surface and transferring the articles to the receiving surface. More specifically, the invention relates to cutting discrete strips of continuously moving endless ribbon material, rotating the strips, and transferring the strips to a sheet of continuously moving material with the lengths of the strips in a direction transverse to the direction of movement of the sheet.

BACKGROUND OF THE INVENTION

The desirability of applying elastic in the waist areas of various types of garments to assist in fitting of the garments is well known. The traditional method of securing elastic to a garment is by sewing the elastic to the garment material. The material is either gathered and the elastic is applied in a relaxed condition or the material is maintained flat and the elastic is applied in a stretched condition. The sewing of the elastic to the garment material, whether the sewing is done by hand or by machine, is slow and therefore costly in terms of the labor required.

In relatively modern technology relating to disposable garments, elastic strip material has been bonded to sheet material by the use of adhesives or heat bonding. These approaches have been commercially successful where the elastic strips have been applied with their lengths in the direction of movement of the sheet material from which the garment is formed. However, efforts to apply elastic strip material with all or a portion of its length transverse to the direction of movement of the garment sheet material have not been as successful. Examples of these approaches are illustrated in Rega U.S. Pat. No. 4,285,747 and Bourgeois U.S. Pat. No. 3,828,367. The Rega patent discloses the application of an unstretched elastic strip to a continuously moving web in a direction transverse to the direction of movement of the web and across a longitudinal tuck in the web. After application of the strip to the web, the web is extended in the lateral direction to remove the tuck and stretch the strip so that the web is elasticized in the area of the strip. In the Bourgeois patent, continuous elastic ribbon in a stretched condition is fed into grooves in a roll. The grooves are disposed in a direction transverse to the direction of a continuous web moving under the roll. As the web moves under the roll, the stretched elastic is applied to the web to elasticize the web in the areas of the ribbon.

In another area of prior art relevant to the present invention, apparatus has been developed for rotating strip material and applying it to sheet material in a direction transverse to the direction of movement of the latter. Also, apparatus has been developed for rotating objects from one orientation to another while the objects are moving from a receiving station to a delivery station of the apparatus. U.S. Pat. Nos. 3,728,191 to Wierzba et al and 4,394,898 to Campbell disclose examples of these types of apparatus. The Wierzba patent relates to the attaching of an adhesive tape to a web which ultimately forms part of a disposable diaper. The tape is used to fasten the waist of the diaper. An endless length of the tape material is continuously fed onto a platen mounted on a revolving roll. A strip of the tape is cut from the endless length by a cutting blade which engages the tape and an anvil mounted on the frame of the roll. The platen is rotated by a cam drive mechanism utilizing a cam surface mounted separately from the roll on the frame of the apparatus. The platen rotates the severed strip while carrying it to a transferring station where the strip is applied to a web with the length of the strip transverse to the direction of movement of the web.

In the Campbell patent, a series of diapers are fed onto rotatable platens mounted on a continuously revolving roll. Alternating ones of the platens are rotated 90° in opposite directions so that alternating diapers carried by the platens are correspondingly rotated. The alternately rotated diapers are carried on the platens and delivered to a receiving conveyor. The platens are rotated by a cam drive mechanism having a cam control surface mounted externally of the revolving roll in a stationary manner on the frame of the apparatus.

A problem with the apparatus disclosed in the Wierzba patent is that, due to the force of the cutting blade against the tape and the anvil on the frame of the roll, the severed end of the tape strip may be temporarily welded to the anvil. The extent of the welding problem will depend in part on the material characteristics of the tape, e.g., the flexibility and softness or brittleness of the tape material. The consequence of the welding of the tape strip to the anvil is that, upon rotation of the platen and the strip, the strip will not rotate with the platen and will be moved laterally out of place due to its severed end remaining welded to the anvil on the frame. The cam drive arrangements of the Wierzba and Campbell patents require, particularly where the roll and the platen are moving at relatively high speeds, lubrication of the cam surface used to control the drive means. The material carried by the roll will consequently be exposed to the dirt and grime which commonly accompanies lubricants.

The applicant's invention is an improvement over the apparatus of the Wierzba and Campbell patents and, in particular, over the apparatus disclosed in the Wierzba patent.

SUMMARY OF THE INVENTION

It is a general object of this invention to provide an apparatus in which an article is carried on a revolving roll and, while being carried, is rotated by means mounted entirely on the roll from a first orientation to a second orientation and transferred on to a continuously moving receiving surface.

Another object of the invention is to provide an apparatus in which a continuously moving length of material is supplied to a platen means carried on a revolving roll toward a continuously moving endless sheet of material, a discrete strip of material is severed on the platen means from the length of material, the platen means is rotated while being carried on the roll to rotate the strip to a position in which the length of the strip is transverse to the direction of movement of the sheet material, and the strip is applied to the moving sheet material in the transverse position.

Another object of the invention is to provide an apparatus in which a continuously moving length of material is supplied to a platen means carried on a revolving roll toward a continuously moving endless sheet of material, a discrete strip of material is severed on the platen means from the length of material by applying force to the length of material against an anvil mounted on the platen means, the platen means is rotated while being carried on the roll to rotate the strip to a position in which the length of the strip is transverse to the direction of movement of the sheet material, and the strip is applied to the moving sheet material in the transverse position.

Another object of the invention is to provide an apparatus in which an endless length of material is continuously fed into engagement with a rotatable platen means mounted on a revolving roll, a discrete length of the endless material is severed by applying severing force to the material and to the platen means, the platen means is rotated with a rotating drive means, and a space is provided between the platen means and the rotating drive means in the direction of the severing force applied to the platen means to prevent transmittal of the force from the platen means to the rotating drive means.

A further object of the invention is to provide an apparatus in which an endless length of ribbon material is continuously fed into engagement with a rotatable platen means mounted on a revolving roll and rotated by a drive means entirely mounted on the roll, a discrete strip of ribbon material is severed on the platen means by applying severing force to the ribbon material and a cutting surface on the platen means with a cutting means, the platen means is carried on the revolving roll toward a continuously moving endless sheet of material and, while being carried, the platen means is rotated to thereby rotate the discrete strip, and the discrete strip of material is transferred to the sheet with the length of the discrete strip transverse to the direction of movement of the sheet.

The invention is carried out by providing an apparatus having a revolving roll, platen means rotatably supported on the roll for receiving an endless length of material and carrying and transferring discrete strips of the material to a moving receiving surface, cutting means engaging the endless material on a cutting surface of the platen means to sever the discrete strips from the endless material, and rotating drive means mounted entirely on the roll for rotating the platen means to thereby rotate the discrete strips, while they are carried by the platen means, to a position transverse to the direction of movement of the receiving surface.

The endless length of material is continuously fed at a feed station on to a platen means mounted on the revolving roll. The receiving surface is continuously moved to the roll at a transferring station where the receiving surface engages the platen means and the discrete strips are transferred from the platen means to the receiving surface. A retaining means, which may comprise a vacuum system, applies force to hold the discrete strips on the platen means while they are being severed from the endless length of material and until they are transferred to the receiving surface. An anvil may be mounted on the platen means. The endless material, when on the platen means, engages the anvil. The cutting means moves through the endless material and against the anvil to sever the discrete lengths of material on the platen means. As a consequence of the engagement of the cutting means with the anvil, the severing force of the cutting means is applied to the anvil and transmitted from the anvil to the platen means. The platen means is supported directly on the roll such that the severing force transmitted to the platen means is, in turn, transmitted to the roll. However, the rotating drive means is spaced from the platen means in the direction of the severing force applied by the cutting means such that the severing force is not transmitted from the platen means to the rotating drive means to stress the various components of the drive means.

BRIEF DESCRIPTION OF THE DRAWINGS

Further objects and advantages of the invention will appear when taken in conjunction with the accompanying drawings, in which.

DETAILED DESCRIPTION OF THE INVENTION

Figures 1A, 1B:
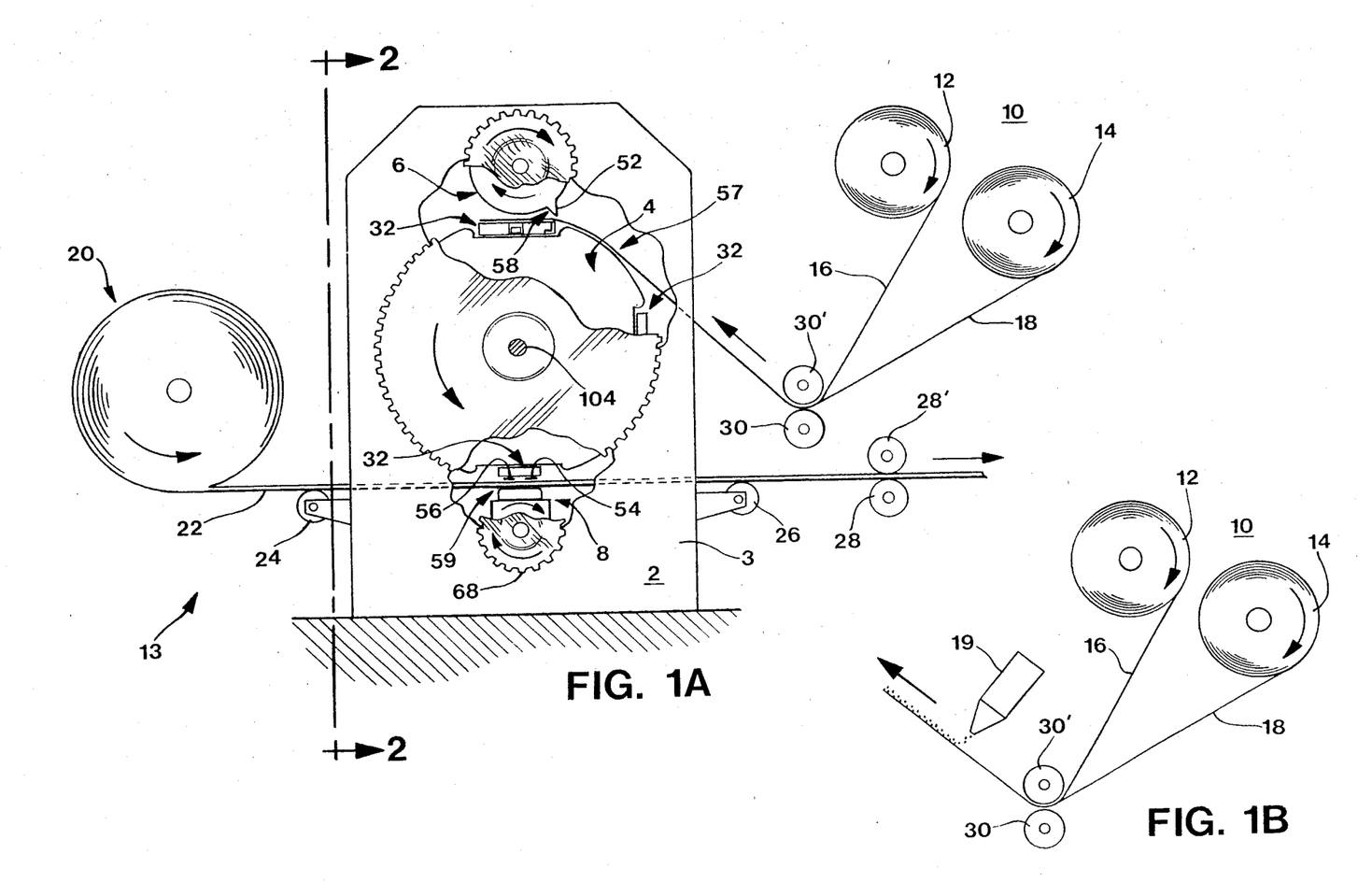
FIG. 1A is a side elevation view of a ribbon supply means, a sheet supply means and the revolving roll apparatus of the invention.
FIG. 1B is a side elevation view of an alternate embodiment of the ribbon supply means.
Figure 2:
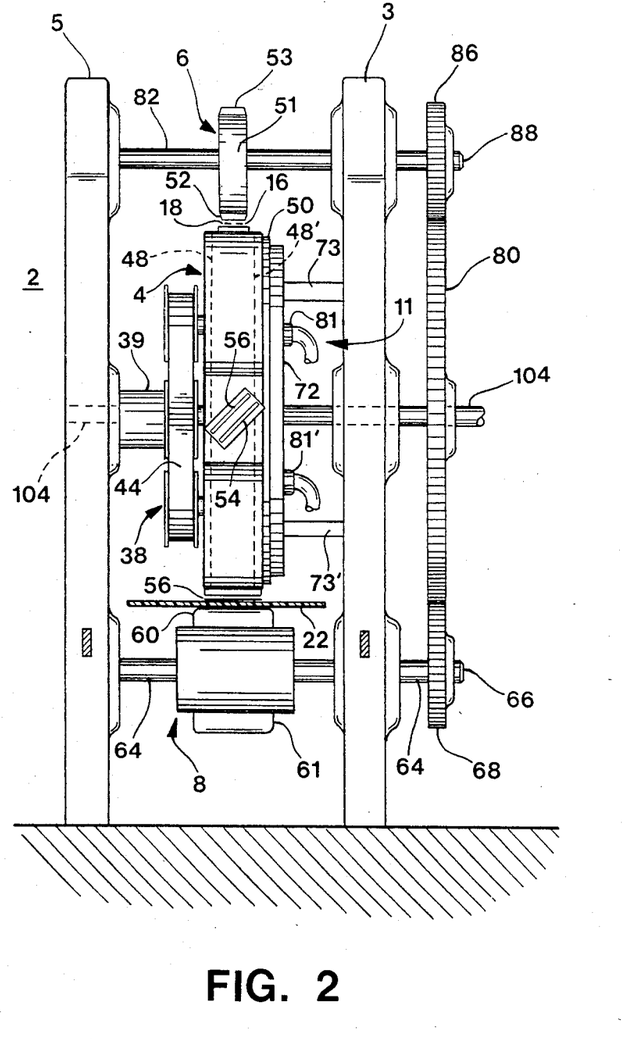
FIG. 2 is an elevation view of the revolving roll apparatus of the invention taken along the lines 2—2 of FIG. 1A.

Referring generally to FIGS. 1A and 2, the apparatus of the invention is shown as having a frame 2, on which a revolving roll 4 is mounted. A cutting roll 6 and an applicator means 8 are rotatably mounted on frame 2 at upper and lower areas of the frame. Endless ribbon material supply means 10 including ribbon supply rolls 12 and 14 rotatably supported on a suitable means (not shown) are provided for continuously supplying ribbons 16 and 18 to the revolving roll 4. The ribbons 16 and 18 are fed to the roll 4 and the rolls 12 and 14 rotate in the directions shown by the arrows in FIG. 1A. A sheet supply means 13 including a web or sheet supply roll 20 rotatably supported by suitable means (not shown) is provided for continuously feeding an endless sheet or web of material 22 into engagement with the revolving roll 4 between the roll and the applicator means 8.

The roll 4 is mounted on the revolving drive shaft 104 between the spaced side walls 3 and 5 of the frame 2. The shaft 104 is journalled in bearings (not shown) on walls 3 and 5. The shaft 104 projects through the wall 3 and is rotatably driven to revolve the roll 4 in a continuous manner by a suitable drive source (not shown). The roll 4 comprises a pair of spaced apart side plates 48, 48' affixed to the shaft 104 and a plurality of slip plates 98 (see FIGS. 3A and 3B) positioned at equal distances about the circumference of the roll 4. The slip plates span and are affixed to each of the side plates 48, 48'.

Each of the slip plates have an outward facing surface 100. Vacuum plates 78 are positioned between each adjacent pair of slip plates, as illustrated in FIG. 3B, and are also affixed to each of the side plates 48, 48'. As the roll 4 revolves each full revolution, it sequentially passes through a feed station 57, a cutting station 58, and a transferring station 59.

Figure 3A:
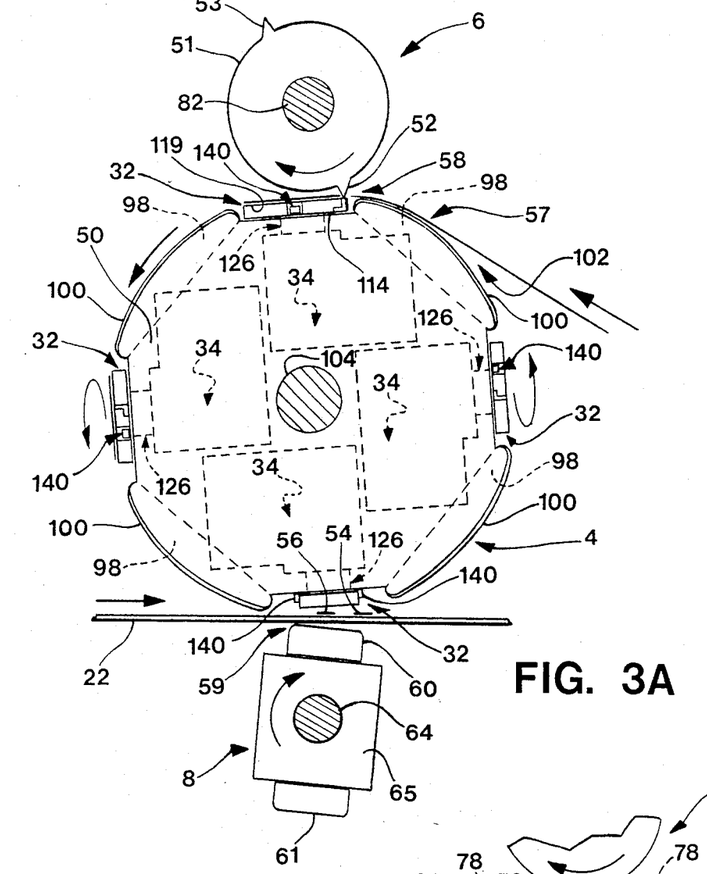
FIG. 3A is a side elevation view of the revolving roll according to the invention.
Figure 3B:
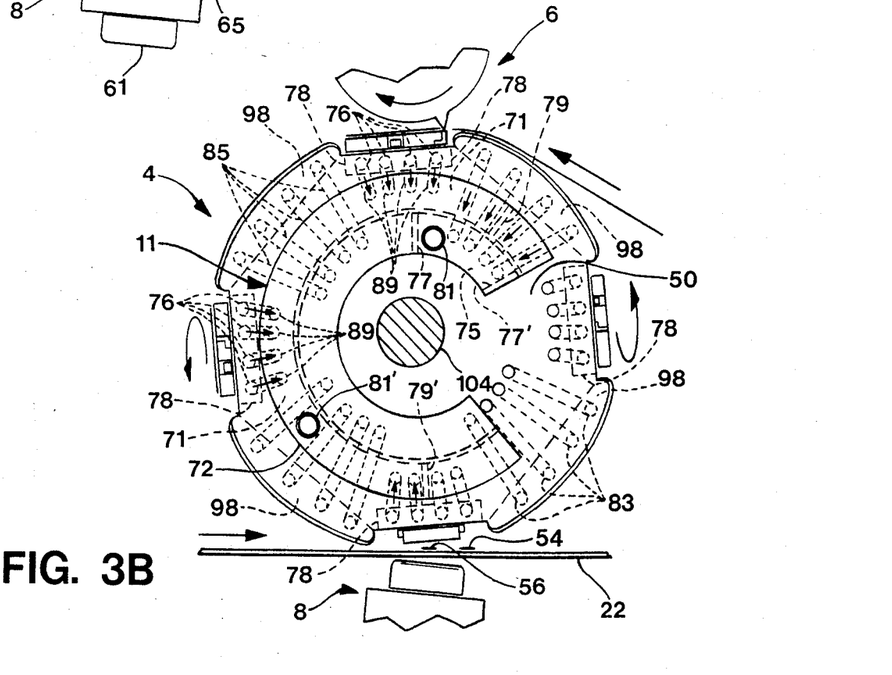
FIG. 3B is a side elevation view of the revolving roll illustrating a vacuum system for holding the ribbon and ribbon strips on the roll.

Mounted on the roll 4 are a plurality of rotatable platen means 32, as shown in FIGS. 3A and 3B, for receiving the endless ribbons 16 and 18, carrying discrete ribbon strips 54 and 56 (see FIGS. 1A and 2), and transferring the strips 54 and 56 to the sheet 22. Each platen means 32 is directly mounted on a vacuum plate 78 between each adjacent pair of slip plates along the circumference of the roll 4. The slip plates 98 and the platen means 32 together form the outer circumferential surface 102 of the roll 4. The platen means 32 are rotatable about axes that lie in a direction transverse and preferably perpendicular to the direction of the axis of the roll 4. In the embodiment of the invention illustrated in FIG. 3A, the rotational axis of the platen means 32 also lie along lines radially extending from the axes of the roll 4. Because the platen means bear directly against the vacuum plates on which they are mounted, when the platen means are rotated, they will slidably move along the surfaces of the vacuum plates.

One of the plurality of rotatable platen means 32 is shown in greater detail in FIGS. 4, 4A, 5 and 6. Each platen means 32 includes a rectangular body 31 (see FIG. 4A) and a circular base 35. The circular base 35 has a pair of openings 147 and 149 extending through at an inward surface 117. The surface 117 faces in the direction of and closes one end of an opening 84 in the vacuum plate 78. The rectangular body 31 has an inward facing surface 114 bearing directly against the vacuum plate 78 on which the platen means 32 is supported. The rectangular body 31 also includes an outward facing cutting surface 119, opposite ends 106 and 108 and lateral bearing surfaces 146 and 148. An anvil 122 may be mounted on the rectangular body 31 at its end 106 and form a portion of the outer surface 119 of the rectangular body member 31. Formed lengthwise along the surface 119 of the rectangular body 31 are grooves 116 and 118 for distributing vacuum pressure admitted through the vacuum passages 74. The vacuum passages 74, which pass through the platen member 33, will be described in greater detail hereinafter. The platen means 32 also includes a screen 115 positioned over the outer surface 119 of the rectangular body 31 for assisting in distributing vacuum pressure along the surface.

Figure 4:
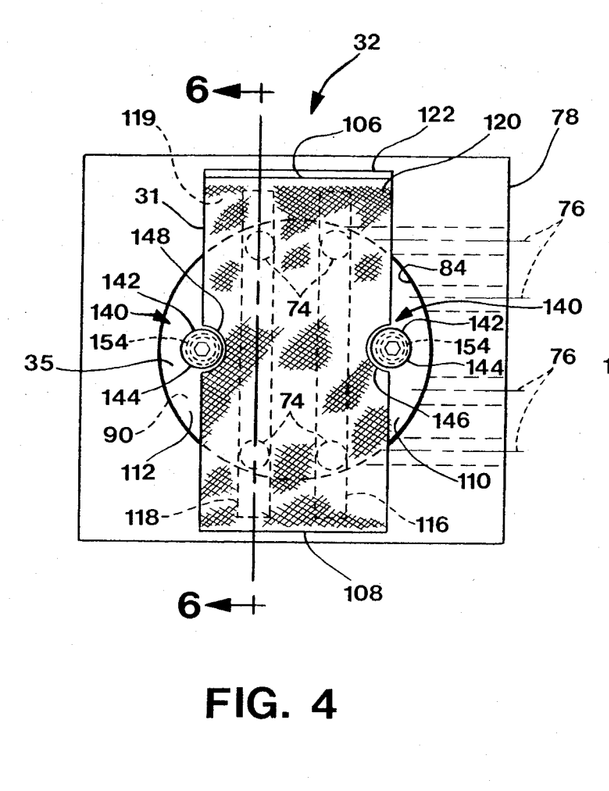
FIG. 4 is a plan view illustrating a rotatable platen means mounted on the roll of FIG. 3A.
Figures 4A, 7, 8, 9, 10:
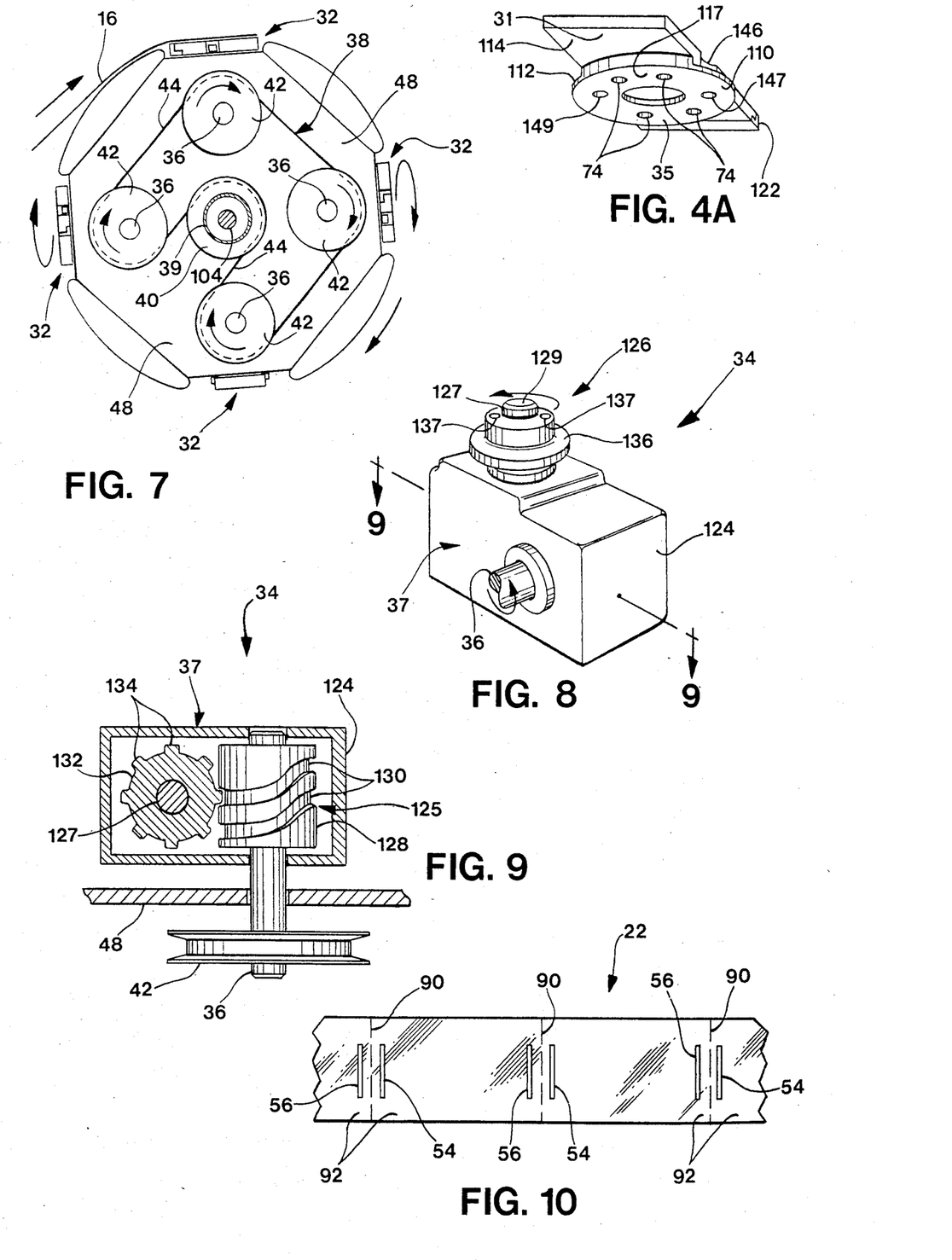
FIG. 4A is a perspective view of the platen means shown in FIG. 4.
FIG. 7 is an elevation view of a belt drive for a rotating means for the platen means.
FIG. 8 is a perspective view of the rotating means for the platen means.
FIG. 9 is a plan view, partially in section, of the rotating means for the platen means.
FIG. 10 is a plan view of an endless sheet of material for use in fabricating a disposable garment.
Figure 5:
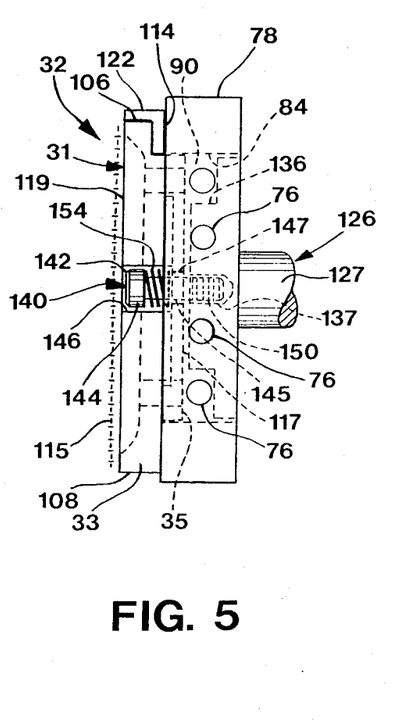
FIG. 5 is a side view of the platen means shown in FIG. 4.
Figure 6:
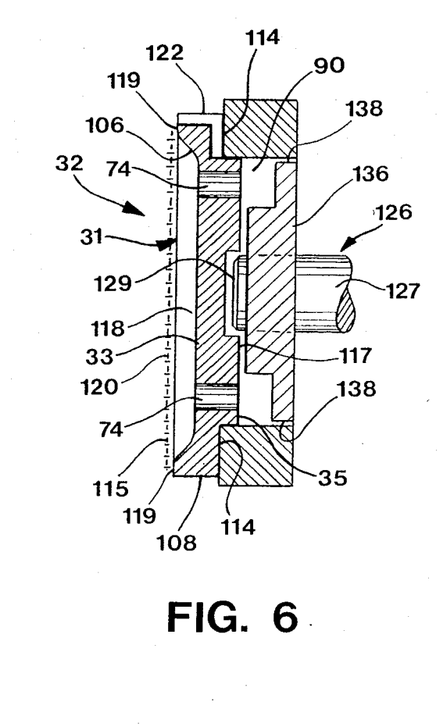
FIG. 6 is a side sectional view of the platen means shown in FIGS. 4 and 5.

With reference to FIGS. 3A, 8 and 9, a plurality of drive means 34 for providing rotating drive force to the platen means 32 are illustrated. Each drive means 34 is entirely mounted on the roll 4 between the side plates 48 and 48' (See FIG. 2). As shown in FIGS. 8 and 9, a drive means 34 includes an input drive shaft 36, cam drive means 37, and output means 126. Each input drive shaft 36 is rotatably driven by a drive source which will be described in detail hereinafter. As shown in FIGS. 3A and 5, each output means 126 extends towards and engages a platen means 32 to rotatably drive the platen means.

The cam drive means 37 is illustrated in FIGS. 8 and 9 in a simplified manner and includes only those components which are necessary for an understanding of its operation in conjunction with the other elements of the present invention. Also, the cam drive means 37 is of a type that is well known and commercially available from various sources such as the Commercial Cam Division of Emerson Electric Company. The cam drive means 37 is entirely mounted on the roll 4 and comprises a housing 124 and a control means 125. The control means 125 comprises a cam cylinder 128 mounted on and rotating with the input drive shaft 36 and having a cam surface or groove 130. A cam follower wheel 132 affixed to the output shaft 127 of the output means 126 includes followers 134 positioned in the cam groove 130 such that the follower wheel 132 is rotated as determined by the direction of the path of the cam groove 130 as the cylinder 128 rotates. It is preferred that each platen means 32 has an intermittent rotating movement in which it does not rotate while at and between feed and cutting stations 57 and 58 and while at the transferring station 59. The platen means 32 should be stationary at these stations to avoid movement of the ribbons 16 and 18 or the strips 54 and 56 that interferes with the positioning and cutting of the strips on the platen means 32 or their transfer in the correct transverse position to the sheet 22. Further, with reference to FIGS. 1A, 2 and 3A, the platen means 32 should be maintained at the feed and cutting stations in a first orientation in which the rectangular body 31 has its length and the vacuum grooves 116 and 118 in alignment with the feed direction of the ribbons 16 and 18 while at the feed and cutting stations. On the other hand, while the platen means 32 is at the transferring station 59, it should be in a second orientation in which the length of the rectangular body 31 is at a transverse 90° angle to the direction of movement of the sheet 22. The intermittent rotation and positioning requirements of the platen means 32 is accomplished by providing the necessary angle in the pitch of the cam groove 130. During the time period in which the cam follower wheel 132 and therefore the platen means 32 are not to move, the portion of the cam groove 130 engaging a cam follower 134 has a pitch angle of 0°. During the time period in which the cam follower wheel 132 is to rotate such that the platen means 32 rotates from the first position at the cutting station 58 to the second position at the transferring station 59, the cam groove 130 has a pitch such that the cam followers 134 advance in an axial direction within the groove 130 to provide the desired rotation to the platen means 32. The particular required pitch angle of the groove 130 is determined by the speed and distances of travel of the various components of the apparatus.

The output means 126 of rotating drive means 34 includes an adaptor plate 136 (FIG. 8) affixed to an output shaft 127 exterior of the housing 124. The adaptor plate 136 is positioned on the shaft 127 such that it rotates in a plane generally parallel to the outward surface 119 (See FIG. 6) of the rectangular body member 31. The adaptor plate 136 as well as the end 129 of the shaft 127 extend toward but are spaced from the inner surfaces 114 and 117 of the rectangular body 31 and circular base 35, respectively. Thus, upon the severing of the ribbons 16 and 18 (See FIGS. 1A, 4, 5, 6) as described in detail hereinafter, the ribbon severing force of the cutting roll 6 in the direction from the outward surface 119 to the inside surface 114 of the rectangular body 31 and toward the rotating drive means 34, which is applied to the anvil 122 and transferred to the platen means 32, is not transferred via the shaft 127 or adaptor plate 136 to the cam drive means 33. Consequently, wear on the cam drive means 33 due to cutting impact will be avoided and the life of the cam drive means 33 will be substantially longer than otherwise possible.

In FIG. 3A, a plurality of force transferring means 140 are shown in engagement with platen means 32. As illustrated in FIGS. 4 and 5, each force transferring means 140 comprises a part of the output means 126 of the rotating drive means 34 for transferring the rotating force of the cam drive means 37 to the platen means 32. The force transferring means 140 comprises a pair of shoulder bolts 142 each having a head member 144, an elongated shank 145 having a threaded end 150 threadably inserted in threaded opening 137 of the adaptor plate 136, and a spring 154 concentrically mounted in compression on the shank 145 between the head member 144 of the bolt 142 and the circular base 35 of the platen means 32.

The head members 144 of bolts 142, which bear against the lateral surfaces 146 and 148 of rectangular body 31, transfer rotating force of the cam drive means 37 to the rectangular body 31 to rotate the platen means 32. Since the adaptor plate 136 on which the force transferring means 140 is mounted rotates in a plane parallel to the outward surface 119 of the rectangular body 31, the rotating force of the force transferring means 140 will be applied in a direction parallel to the plane of the outward surface 119. Conversely, rotating force in an opposite direction and in the same plane can also be applied by the platen means 32 to the force transferring means 140. Consequently, since the severing force of the cutting roll 6 is applied in a direction generally transverse to and preferably perpendicular to the plane of the surface 119, the severing force will not be transmitted to the force transferring means 140 and thereby to the cam means 37. The shoulder bolts 142 extend freely through the openings 147 and 149 in the circular base 35 without attachment to the base 35. Consequently, the platen means 32 and drive means 34 are movable relative to each other in the longitudinal dimension of the bolts 142. Thus, the severing force of the cutting roll 6 applied to the platen means 32 in the direction of the drive means 34 will not be transmitted through the force transferring means 140 along the length of the shoulder bolts 142 to the adaptor plate 136 and to the cam drive means 34. This mode of operation of the force transferring means 140 as described above further assists in the avoidance of wear on the cam drive means 33.

As previously described, the platen means 32 engages and slidably rotates on the vacuum plate 78. The compression of the spring 154 between the head member 144 of the bolt 142 and the circular base 33 provides biasing force maintaining the platen means 32 in engagement with the vacuum plate 78 as the platen means 32 rotates. The spring 154 thus functions to hold the platen means 32 on the vacuum plate 78 as the platen means 32 revolves with the roll 4 while at the same time permitting the platen means 32 to rotate in sliding engagement with the vacuum plate 78.

Referring now to FIGS. 2 and 7, a belt drive means 38 for providing rotating drive motion to each of the rotating drive means 34 is illustrated. The belt drive means 38 includes rotating drive pulleys 42 and a stationary pulley 40. The pulley 40 is supported on a cylindrical arm 39 which is mounted on side wall 5 of frame 2. The rotating drive pulleys 42 are mounted on the input shafts 36 of the rotating drive means 34. A continuous drive belt 44 is wrapped around the pulleys 42 and around the stationary pulley as shown in FIG. 7. As the shafts 36 and rotatable pulleys 42 revolve with the roll 4, the belt 44 will move over the surface of the pulley 40 to thereby cause the pulleys 42 to rotate. The input shafts 36 are thus rotatably driven in the direction of the arrows shown in FIG. 7.

Referring again to FIGS. 1A, 2 and 3A, the ribbon supply means 10 feeds the two ribbons 16 and 18 toward the roll 4 and on to the plates 98 over which the ribbons slip as they are initially received on the plates. The ribbons are fed parallel to each other and spaced apart at the distance shown in FIG. 2. The ribbons 16 and 18 are driven towards the roll 4 by drive rolls 30, 30' at speeds such that they move on to the roll 4 under minimal tension in a relatively relaxed condition. The ribbons 16 and 18 may have a coating of pressure sensitive adhesive on their surfaces which face outward of the roll 4. Thus, as discrete lengths of the ribbons 16 and 18 engage sheet 22, as described hereinafter in detail, the discrete lengths will transfer and bond to the sheet 22. Alternatively, with reference to FIG. 1B, the ribbons 16 and 18 may be supplied without an adhesive. The adhesive may then be applied to the ribbons as one of the steps in feeding the ribbons to the roll 4. In FIG. 1B, the ribbons 16 and 18 are shown as being supplied by ribbon feed rolls 12 and 14 to the roll 4 by drive rolls 30, 30'. Between the location of the rolls 30, 30' and the area of engagement of the ribbons 16 and 18 with the roll 4, adhesive is applied to each of the ribbons 16 and 18 by adhesive applicator means 19.

A ribbon and strip retainer means comprising a vacuum system 11 is shown in FIGS. 2 and 3B. The vacuum system 11 includes a side plate 50 affixed to and revolving with the roll 4 and a vacuum cover 72 mounted in a stationary manner on arms 73, 73' extending from side wall 3 of the frame 2. Two vacuum supply passages 81, 81' are connected to the vacuum cover 72 and to a suitable source of vacuum pressure (not shown). The side plate 50 forms the inside wall of a vacuum chamber and the vacuum cover 72 forms the outside wall of the chamber. The cover 72 and the plate 50 are positioned with a very small clearance between them to avoid friction as the plate 50 rotates, but at the same time minimize the loss of vacuum pressure from within the chamber. The interior of the vacuum cover 72 is divided into two semi-circular chambers 71 and 75. The end plugs 77 and 77' form a relatively short chamber 75 which is connected to the vacuum pressure source through the vacuum passage 81. The vacuum chamber 71 is closed at its ends by plugs 79 and 79' and is supplied from the vacuum pressure source through passage 81'. Four vacuum passages 89 for each platen means 32 extend through the plate 50 from the vacuum chamber 71 and connect to vacuum passages 76 in the vacuum plates 78. In FIGS. 4 and 5, the vacuum passages 76 are shown in vacuum plate 78 as connecting with a vacuum chamber 90 formed by the opening 84 in the vacuum plate 78, the inner surface 117 of the circular base 35, and the adaptor plate 136. Since the vacuum openings 74 in the rectangular body 31 are also connected to the vacuum chamber 90, the vacuum pressure from the passages 76 will be applied through the passages 74 and along the grooves 116 and 118 to hold the discrete strips of ribbon 54 and 56 in place on the platen means 32 as will be discussed in detail hereinafter.

As the platen means 32 and the plate 50 revolve on the roll 4, the vacuum passages 89 are connected to the vacuum chamber 71 to thereby provide vacuum pressure to the platen means 32 from the cutting station 58 to the transferring station 59. When each of the platen means 32 rotates outside of the arcuate path between plugs 79 and 79' of the vacuum chamber 71 between the transferring station 59 and the feed station 57, the passages 89 supplying vacuum pressure to that platen means will be exposed to atmospheric pressure and the vacuum pressure to the platen means will terminate. The slip plates 98 each contain vacuum passages 83 connected to their outward surfaces 100. The vacuum passages 85 in the plate 50 connect the vacuum chamber 75 to the vacuum passages 83 in the slip plates. As the slip plates 98 revolve with the plate 50 on the roll 4, the passages 85 move through the vacuum chamber 75 and connect vacuum pressure to the passages 83 in the slip plates 98. Since the vacuum chamber 75 comprises a relatively short portion of the total circumferential length of the cover 72 in the area of feed station 57 and cutting station 58, vacuum pressure will be applied to the slip plates 98 only during the correspondingly short portion of the total circular movement of the passages 85. During the balance of the circular movement of the passages 85, they will be open to the atmosphere. Thus, while the ribbons 16 and 18 are on the slip plates 98 and moving toward the feed station 58, they are held on the slip plates by vacuum pressure from passages 83.

With reference to FIGS. 1A, 2 and 3A, the cutting roll 6 is shown positioned between side walls 3 and 5 of the frame 2 immediately above the revolving roll 4. The cutting roll 6 is supported on a rotatable shaft 82 journalled in bearings (not shown) on walls 3 and 5. The shaft 82 has an end 88 extending through the wall 3 on which a gear wheel 86 is mounted in engagement with a gear wheel 80. The gear wheel 80, in turn, is mounted on shaft 104 to which a rotating drive source is connected, as previously described. Rotatable driving force is thus provided to the cutting roll 6 by the shaft 104 through gears 80 and 86 and shaft 82. The cutting roll 6 includes a cutting wheel 51 having cutting blades 52 and 53 mounted thereon. The cutting blades 52 and 53 are rotated in the direction of the arrow shown in FIG. 1A into engagement, at the cutting station 58, with the ribbons 16 and 18 and the outward surface 119 of the platen means 32 or the anvil 122 mounted on the platen means. Preferably, the anvil 122 is utilized as the severing support surface. Discrete ribbon strips 54 and 56 are thus severed on the platen means 32 from the endless ribbon material 16 and 18. Each blade simultaneously severs the two strips 54 and 56 during each movement through the cutting station 58. Since the strips 54 and 56 are severed on the anvil 122 mounted on the platen means 32, any welding of the ends of the strips 54 and 56 on the anvil 122 as a result of the severing impact will not cause the strips 54 and 56 to be pulled out of position laterally as the platen means 32 rotates. After the severing of the strips 54 and 56, the platen means 32 carries the strips from the cutting station 58 to the transferring station 59.

Since the platen means 32 engage and are directly supported on the vacuum plates 78 of the roll 4, the force of the cutting blades 52 and 53 on the platen means will be largely transmitted to and absorbed by the roll 4. Moreover, the severing force of the cutting roll 6 is in a direction generally transverse to and preferably perpendicular to the plane in which the force transferring means 140 of the cam drive means 37 receives force. Therefore, the severing force will not be transferred to the force transferring means 140 and thence to the cam drive means 37. Also, since the platen means 32 and the force transferring means 140 are moveable relative to each other in the direction of the longitudinal dimension of the bolts 142 of the force transferring means 140, the severing force of the cutting roll 6 which is parallel to the length of the bolts 142 will not be transferred to the cam drive means 37.

The sheet supply means 13, illustrated in FIG. 1A, includes a sheet supply roll 20, the support rolls 24 and 26 mounted on the frame 2, and pull rolls 28, 28'. The rolls 28, 28' pull the sheet 22 to feed it through the transferring station 59 between the roll 4 and the applicator means 8 at a linear speed equal to that of the peripheral speed of the roll 4. The supply roll 20 and the sheet 22 move in the direction of the arrows shown in FIG. 1A. The sheet 22 is supported as it approaches the transferring station 59 by the support roll 24 and is supported as it leaves the transferring station 59 and exits the frame 2 by support roll 26.

The applicator means 8, illustrated in FIGS. 1A, 2, and 3A, is positioned between the walls 3 and 5 of frame 2 and is mounted on rotatable shaft 64. The shaft 64 is journalled in bearings (not shown) on walls 3 and 5 and has an end 66 extending through the wall 3. A gear wheel 68 is affixed to the end 66 of the shaft 64 and is positioned in engagement with the gear wheel 80 mounted on the roll drive shaft 104. The drive source connected to the shaft 104 thus provides rotating movement to the applicator means 8 through the gear wheels 80 and 68 and the shaft 64. The rotation of the applicator means 8 is in the direction of the arrow shown in FIG. 1A. The applicator means 8 includes a body 65 through which the shaft 64 passes and striking members 60 and 61 comprising a resilient material such as rubber. The striking members 60 and 61 are rotated by the applicator means 8 alternatingly into engagement with the endless sheet 22 to press the sheet against the platen means 32. Since the strips 54 and 56 have an adhesive coating on their sides facing outward of the roll 4 and thus toward the sheet 22 at the station 59, the compression of the sheet 22 against the platen means will cause the strips 54 and 56 to transfer from the platen means and adhere to the sheet due to the adhesive on the strips. The applicator means 8 is shown in FIG. 2 with its striking member 60 centered below a platen means at the transferring station 59. In FIG. 3A, the applicator means 8 is shown as its striking member 60 moves away from the transferring station 59 after the discrete strips 54 and 56 have been transferred to the sheet 22.

To summarize the operation of the apparatus disclosed herein, endless lengths of flexible material such as ribbons 16 and 18 are continuously fed from the rolls 12 and 14 through the drive rolls 30, 30' in a relatively relaxed, unextended condition into engagement with the revolving roll 4. As the ribbons 16 and 18 engage the roll 4, they slide over a slip plates 98 and on to a platen means 32. The ribbons are held on the plate 98 from moving laterally out of a path in the direction of their feeding movement to the roll 4 by vacuum pressure applied through vacuum passages 83 in the plate 98. Also, as the ribbons move on to the platen means 32 at the feed station 57, vacuum pressure from the grooves 116 and 118 in the platen means 32 assists in maintaining the ribbons aligned with their feed path. At the feed station 57 and cutting stations 58, the platen means 32 is in its first orientation in which the length of rectangular body 31 and the grooves 116 and 118 are in alignment with the feed direction of the ribbons 16 and 18. The vacuum pressure continues to be applied through the grooves 116 and 118 to hold the severed strips 54 and 56 to the platen means 32 while the platen means 32 revolves from the cutting station 58 to the transferring station 59. As each platen means 32 moves with the roll 4 to the cutting station 58, the cutting roll 6 rotates one of the blades 52 or 53 into engagement with and through the ribbons 16 and 18 and into engagement with the anvil 122 to sever discrete strips of ribbon 54 and 56 on the platen means 32 from the continuous ribbons 16 and 18. The severing force of the cutting blades applied to the anvil 122 and transmitted to the platen means 32 in the direction of the cam drive means 37 is not transferred to the cam drive means 37 due to the spacing of the latter from the platen means 32 and the relative movability of the rotating force transfer means 140 and the platen means 32. Also, the supporting of the platen means 32 on the vacuum plate 78 of the roll 4 results in the absorbing of much of the severing force by the roll 4.

As the roll 4 revolves the platen means 32 away from the cutting station 58, the cam drive means 37 begins to rotate the output means 126 to thereby apply rotating force to the platen means 32 through the shoulder bolts 142 of the force transferring means 140. A partially rotated position of the platen means is illustrated by platen means 32 in FIGS. 2 and 3A intermediate the cutting station 58 and the transferring station 59. As the roll 4 continues to revolve toward the transferring station 59, the platen means 32 also continues to rotate the discrete strips 54 and 56. As the platen means arrives at the transferring station 59, the cam drive means 37 has rotated the platen means 32 to its second orientation in which the length of the rectangular body 31 has a position at a 90° transverse angle to the direction of movement of the sheet 22. Therefore, the discrete strips 54 and 56 will also have been rotated to a 90° transverse position prior to the transfer of the strips to the endless sheet 22. Due to the compression of the strips 54 and 56 against the sheet 22 caused by the engagement of the sheet 22 by one of the striking members 60 or 61 of the applicator means 8, the strips will adhere and transfer to the sheet. Also, at this point in the revolvement of the roll 4, to assist in the transfer of the strips 54 and 56 to the endless sheet 22, the vacuum force applied to the strips 54 and 56 through the grooves 116 and 118 of the platen means is terminated due to the ending of the vacuum chamber 71 by the plug 79'.

After the strips 54 and 56 have been transferred to the endless sheet 22, the cam drive means 37 applies rotational force to the platen means 32 through the force transferring means 140 in a direction opposite to that of the force applied as the roll 4 moved from the cutting station 58 to the transferring station 59. The platen means 32 is thus rotated, prior to its reaching the feed station 57, back to its first orientation in which the vacuum grooves 116 and 118 are aligned with the path of the feeding of the continuous ribbons 16 and 18.

Where the composite endless sheet 22 and discrete strips 54 and 56 are to be utilized in the fabrication of a disposable garment, after the endless sheet 22 leaves the transfer station 59, it may be severed across it full width along the dotted lines 90 shown in FIG. 10. This severing operation will produce separate blanks 92 for use in a disposable garment such as a disposable diaper. The ends of the blanks 90, where the strips 54 and 56 are located, will ultimately become the front and rear waist areas of the disposable garment. The sheet material 22 in this use of the apparatus is preferably a material such as polyethylene film. Where the ribbon strips 54 and 56 are of a material that may have its characteristics modified such that the strips become elastic in nature, for example, by subjecting the strips to heat, the strips may be heated at a suitable point after they have been applied to the sheet 22 to thereby elasticize the waist portions of the garment. Other steps may also be performed, either before or after the severing of the sheet, to provide additional components to complete the disposable garment.

As previously described, the discrete strips 54 and 56 may be rotated to a 90° transverse angle relative to the direction of movement of the sheet 22 and transferred to the sheet 22. A 90° transverse angle is most desirable where the sheet 22 is to be used in fabricating disposable garments and the strips 54 and 56 are to provide elasticization of the waist areas of the garments. However, if it is desired to carry and transfer other types of materials utilizing the apparatus of the invention, the transverse position of such materials relative to their position when initially received on the platen means or relative to the direction of movement of the receiving surface onto which they are transferred may be at an angle other than 90°. Thus, the term "transverse" as used in this context may be considered to mean any orientation of the rotated article which is at an angle relative to the position of the article prior to its rotation of the roll on the invention.

An apparatus and method has been disclosed in which an article may be moved at a first station on to a rotatable platen means mounted on a revolving roll, held on the platen means while being rotated to a different position relative to that at which the article was received on the platen means, and transferred at a second station on to a sheet or other receiving surface at the new relative angular position of the article. Where it is desired to transfer an endless length of material to the platen means and sever discrete pieces of the material to be carried and transferred by the platen means, an anvil is provided on the platen means and cutting means are provided to sever discrete pieces of the material on the platen means. The discrete pieces are held and rotated by the platen means as it revolves with the roll and transferred at the second station to a continuously moving receiving surface.

Where the apparatus performs a severing operation, the mounting of an anvil on the platen means is advantageous, particularly when severing light weight, flexible film materials. Such materials will tend to "weld" to the anvil during the severing step. This presents a serious problem in maintaining the desired orientation of the strips of severed material in the feed direction of the endless ribbon material if the anvil is directly mounted on the roll and therefore is stationary while the platen means is rotating. The mounting of the anvil in a stationary manner relative to the platen means will cause the ends of the strips welded to the stationary anvil, upon rotation of the platen means, to remain with the anvil and move the strips being rotated on the platen out of position or cause their stretching and sudden release to further interfere with their proper positioning. Placing the anvil on the rotating platen eliminates this problem.

The apparatus may be utilized to rotate one or multiple strips of material simultaneously and apply them to a receiving surface. Consequently, several strips may be located adjacent each other in a position transverse to the direction of movement of a sheet. In fabricating a garment such as a disposable diaper from the sheet, the ability to position two strips of elastic material on the sheet parallel and close to each other permits simultaneous elasticization of the front and rear waist areas of contiguous diaper blanks.

The rotating drive means for the platen means, i.e., the cam drive means, is entirely mounted on and rotates with the revolving roll. Thus, there is no need to have part of the drive means extend from the roll and engage any stationary mechanism such as a stationary cam surface. The mounting of the cam drive means entirely on the revolving roll eliminates the exposure of the material being handled by the roll apparatus to lubricants required when there is engagement between stationary and moving mechanical parts as in prior art devices.

It will be understood that the foregoing description of the present invention is for purposes of illustration only and that the invention is susceptible to a number of modifications or changes, none of which entail any departure from the spirit and scope of the present invention as defined in the hereto appended claims.

What is claimed is:

1. An apparatus for applying to a sheet of a first material, continuously moving in a first direction, at least one discrete length of a second material, comprising:
   a revolvable roll;
   feeding means for feeding at least one continuous ribbon of said second material into circumferential engagement with said revolvable roll;
   cutting means, with at least one cutting blade, for cutting said continuous ribbon into said at least one discrete length while said ribbon is in engagement with said revolvable roll;
   at least one rotatable platen means, disposed on and perpendicularly movable with respect to the plane of rotation, and revolvable with, said revolvable roll, for rotating said at least one discrete length from a first position to a second position;
   first drive means, disposed within, and revolvable with, said revolvable roll;
   a cutting surface, strikable by said cutting means with a force sufficient to cut said ribbon, disposed on, and rotatable with, said rotatable platen means;
   means for transferring drive from said first drive means to said rotatable platen means in a plane parallel to the plane of said cutting surface; and
   application means for transferring said at least one discrete length from said revolvable roll to said sheet whereby said cutting force is not transmitted to said first drive means.

2. The apparatus of claim 1 further comprising first retaining means for retaining said ribbon in circumferential engagement with said revolvable roll.

3. The apparatus of claim 2 further comprising second retaining means for retaining said at least one discrete length on said rotatable platen means until said discrete length is transferred to said sheet.

4. The apparatus of claim 4 wherein said first and second retaining means comprise first and second vacuum means for providing first and second vacuums to circumferential portions of said revolvable roll and said rotatable platen means respectively.

5. The apparatus of claim 4 wherein said rotatable platen means comprise:
   a first surface providing at least one ribbon receiving area;
   a second surface slidably mounted on a vacuum plate; and
   vacuum communication means for communicating said second vacuum from said second vacuum means to said first surface via said vacuum plate.

6. The apparatus of claim 5 wherein said revolvable roll further comprises a frame and wherein said force diverting means comprises mounting means for mounting said vacuum plate to said frame whereby said force is transferred from said cutting surface to said frame via said vacuum plate.

7. The apparatus of claim 6 wherein said cutting means comprises;
   a cutting roll, with said at least one cutting blade; and
   second drive means for revolving said cutting roll in synchronizm with said revolvable roll whereby said cutting blade cuts said ribbon at said cutting surface on said rotatable platen means.

8. The apparatus of claim 7 wherein said feeding means comprises:
   a supply means for providing a continuous length of said at least one ribbon of said second material; and
   a pair of feed rolls feeding said ribbon circumferentially to said revolving roll with the length of said ribbon coinciding with said first direction.

9. The apparatus of claim 8 wherein said first drive means comprises:
   means for maintaining said rotatable platen means in said first position until said ribbon is received on said first surface and cut by said cutting means;
   means for rotating said rotatable platen means to said second position;
   means for maintaining said rotatable platen means in said second position until said discrete length is transferred to said sheet; and
   means for returning said rotatable platen means to said first position.

10. The apparatus of claim 9 further comprising:
    an applicator roll, with at least one striking member, disposed on an opposing side of said sheet from said revolving roll;
    third drive means for revolving said applicator roll in synchronizm with said revolvable roll, whereby said striking member strikes said sheet at a section of said sheet wherein said discrete length is to be applied, causing said sheet to engage said rotatable platen means whereby said discrete length is transferred to said sheet.

11. The apparatus of claim 10 wherein said first vacuum means further comprises first control means for controlling the application and removal of said first vacuum to and from said circumferential portions of said revolvable roll.

12. The apparatus of claim 11 wherein said second vacuum means further comprises second control means for controlling the application and removal of said second vacuum to and from said first surface of said rotatable platen means.

13. The apparatus of claim 12 wherein said first position of said discrete length comprises a first orientation wherein said discrete length is essentially parallel to said first direction and wherein said second position of said discrete length comprises a second orientation wherein said discrete length is at an angle measured from said first direction.

14. The apparatus of claim 13 wherein said angle is essentially transverse to said first direction.

15. The apparatus of claim 14 wherein said cutting surface further comprises an anvil mounted on and rotatable with said rotatable platen means.

* * * * *